United States Patent [19]

Siedle

[11] Patent Number: 4,788,308

[45] Date of Patent: Nov. 29, 1988

[54] RHODIUM OXYMETALLATE CATALYSTS

[75] Inventor: Allen R. Siedle, Lake Elmo, Minn.

[73] Assignee: Minnesota Mining and Manufacturing Company, St. Paul, Minn.

[21] Appl. No.: 29,435

[22] Filed: Mar. 23, 1987

Related U.S. Application Data

[62] Division of Ser. No. 825,663, Feb. 3, 1986, Pat. No. 4,673,753.

[51] Int. Cl.$^4$ ............ C07F 15/00; C07F 11/00; C07F 5/00; C07F 7/00
[52] U.S. Cl. ..................... 556/15; 556/14; 556/16
[58] Field of Search .................... 556/14, 15, 16

[56] References Cited

U.S. PATENT DOCUMENTS

| | | | |
|---|---|---|---|
| 3,527,809 | 9/1970 | Pruett et al. | 260/604 |
| 3,787,468 | 1/1974 | Kingsley et al. | 260/449 |
| 3,821,311 | 6/1974 | Hughes et al. | 260/604 |
| 3,939,188 | 2/1976 | McVicker | 556/14 X |
| 4,089,881 | 5/1978 | Lukehart | 260/429 |
| 4,124,647 | 11/1978 | McVicker | 568/671 |
| 4,196,136 | 4/1980 | Knoth, Jr. | 260/429 |
| 4,201,714 | 5/1980 | Hughes | 556/14 X |
| 4,201,728 | 5/1980 | Hughes | 556/14 X |
| 4,288,380 | 9/1981 | Billig et al. | 556/14 X |
| 4,301,086 | 11/1981 | Pruett et al. | 260/438.1 |
| 4,302,400 | 11/1981 | McVicker | 260/429 |
| 4,363,764 | 12/1982 | Billig et al. | 260/429 |
| 4,397,788 | 8/1983 | Sakakibara et al. | 556/14 |

OTHER PUBLICATIONS

Homogenous Catalysis, G. W. Parsha—1, Wiley, NY, 1980.

Heteropoly and Isopoly Oxymetallates, M. T. Pope, Springer-Verlag, NY, 1983.

D. E. Hendricksen, C. D. Meyer and R. Eisenberg, Inorg. Chem., 16, 970 (1977).

Schrock and Osborn, J. Am. Chem. Soc., 93, 2397 (1977).

*Primary Examiner*—Paul F. Shaver
*Attorney, Agent, or Firm*—Donald M. Sell; Lorraine R. Sherman

[57] ABSTRACT

Complex rhodium compounds containing rhodium in combination with the ligands carbon monoxide and a plurality of triarylphosphines and have the formulae:

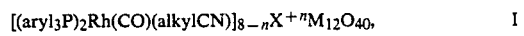

$[(aryl_3P)_2Rh(CO)(alkylCN)]_{8-n}X^{+n}M_{12}O_{40}$,   I

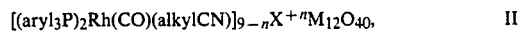
$[(aryl_3P)_2Rh(CO)(alkylCN)]_{9-n}X^{+n}M_{12}O_{40}$,   II

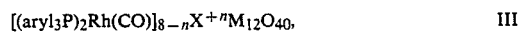
$[(aryl_3P)_2Rh(CO)]_{8-n}X^{+n}M_{12}O_{40}$,   III

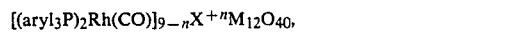
$[(aryl_3P)_2Rh(CO)]_{9-n}X^{+n}M_{12}O_{40}$,   IV

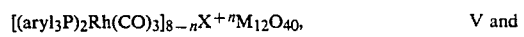
$[(aryl_3P)_2Rh(CO)_3]_{8-n}X^{+n}M_{12}O_{40}$,   V and

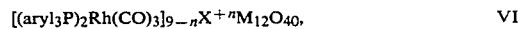
$[(aryl_3P)_2Rh(CO)_3]_{9-n}X^{+n}M_{12}O_{40}$,   VI wherein alkyl is lower alkyl ($C_1$ to $C_4$), X is a transition element selected from Periodic Table groups IIIA, IVA, VA, or VIII, aryl can be phenyl or phenyl substituted by 1 to 3 lower alkyl ($C_1$ to $C_4$) and lower alkoxy ($C_1$ to $C_4$) groups, M is molybdenum (Mo) or tungsten (W), and n is an integer having a value 2 to 5. These novel complex rhodium compounds catalyze the hydroformylation of olefins to provide carboxylic acids, the oxidation of carbon monoxide to form carbon dioxide, the isomerization of terminal to internal olefins and the reduction of nitric oxide to nitrous oxide by carbon monoxide.

6 Claims, No Drawings

RHODIUM OXYMETALLATE CATALYSTS

This is a division of application Ser.No. 825,663 filed Feb. 3, 1986, now U.S. Pat. No. 4,673,753.

FIELD OF THE INVENTION

This invention relates to complex metal oxides containing rhodium and a process for their preparation. The complex compounds are useful as catalysts in organic transformations.

BACKGROUND OF THE INVENTION

Metals, metal salts, and metal complexes, deposited on chemically inert, high surface area carriers such as alumina and silica, are well known catalysts in organic chemistry. Rhodium is a metal often used in catalytic hydrogenation and use of rhodium compounds to activate carbon monoxide in its reactions with organic substrates is also well known; see, U.S. Pat. No. 3,527,809 and G. W. Parshall in "Homogeneous Catalysis", Wiley, N.Y., 1980, p. 85.

Hydroformylation, the addition of hydrogen and carbon monoxide to an olefin to provide an aldehyde, can be catalyzed by rhodium complexed with carbon monoxide and phosphine ligands; see, for example, U.S. Pat. Nos. 4,363,764 and 4,288,380. In U.S. Pat. No. 3,821,311, complex rhodium-containing catalysts have the general formula $[(XRR^1R^2)_mRh(CO)_nY_q]_r$, where m and n may be 0, 1, 2, 3, 4; q is 0, 1 or 3; and r is 1 or 2. X represents P, As or Sb and R, $R^1$, and $R^2$ are alkyl or aryl groups. Y represents hydrogen or electronegative substituents which are anionic when in the free state, i.e. substituents which are formally capable of undergoing nucleophilic substitution reactions, such as halogen, hydroxyl, alkoxyl or acylate, in that they are proton acceptors.

The background art has also taught the deposition of catalysts on inert supports or carriers wherein the carriers do not participate in the catalyzed reaction. Furthermore, the carriers, typically alumina or silica, are generally considered to be polymers comprised of monomeric, repeating, interconnected units, e.g. $Al_2O_3$ or $SiO_2$, respectively. Thus, a single crystal of silica can be considered to be one giant molecule.

Use of certain complex ions or clusters as catalysts is known in the art. These clusters are referred to as heteropolyanions or Keggin ions. They are discrete, charged molecular entities as contrasted with, for example, silica, and have the general formula $X^{+n}M_{12}O_{40}^{-(8-n)}$ where M is molybdenum or tungsten and X is a metallic or metalloid element capable of forming an $XO_4^{-(8-n)}$ oxyanion. The range of X, having formal oxidation number n, is quite large and includes Al, As, B, Co, Cu, Fe, P, Si and Zn. Substitution of some of the Mo or W atoms by other metallic elements, such as vanadium, also leads to clusters in which the basic Keggin ion structure is maintained. One-electron reduction of the $X^{+n}M_{12}O_{40}^{-(8-n)}$ ions by suitable chemical reagents such as $NaBH_4$, sodium amalgam, hydrazine, etc. or by electrochemical means produces the $X^{+n}M_{12}O_{40}^{-(9-n)}$ analogs in which the basic metal oxide cluster structure is also retained. The Keggin ion compounds are reviewed in "Heteropoly and Isopoly Oxymetallates" by M. T. Pope, Springer-Verlag, New York, 1983, pp. 23-27 and pp. 125-127.

Use of mixtures of rhodium and/or platinum with tungsten oxide ($WO_3$) to hydrogenate carbon monoxide to methane is disclosed in U.S. Pat. No. 3,787,468. In these catalysts, the metal oxide serves as an unreactive carrier for the metallic catalyst.

Molecular organometallic compounds, such as those containing the anion $Rh(CO)_2Cl_2^-$, are disclosed by D. E. Hendricksen, C. D. Neyer, and R. Eisenberg, Inorg. Chem., 16,970 (1977) as catalysts in the oxidation of carbon monoxide by nitric oxide according to the equation $$2NO + CO \rightarrow CO_2 + N_2O$$

Schrock and Osborn, J. Am. Chem. Soc., 93, 2397, (1971) especially p. 2401, have prepared salts of $(Ph_3P)_2Rh(CO)_3$ by CO displacement of organic ligands such as cyclooctadiene, bicycloheptadiene and acetone from, e.g., $(Ph_3P)_3Rh(cyclooctadiene)^+$; counterions used are $ClO_4^-$ and $Ph_4B^-$. Simple addition of CO is not suggested.

U.S. Pat. No. 4,196,136 has described two rhodium-containing oxymetallates $$[(CH_3)_3NH]_4[(C_7H_8)_2RhSnPW_{11}O_{39}]$$

$$[(CH_3)_3NH]_4[(Ph_3P)_2RhSnPW_{11}O_{39}]$$

where $C_7H_8$ is bicyclo[2.2.1]heptadiene. In these trimethylammonium salts, the oxymetallate cage is of the general Keggin type but with one of the tungsten atoms replaced by tin. The $(C_7H_8)_2Rh$ and $(Ph_3P)_2Rh$ moieties are connected to the cage by rhodium-tin bonds. These compounds can be distinguished from those of the present invention, which contain neither tin nor Rh—Sn linkages, and thus are fundamentally different.

SUMMARY OF THE INVENTION

The present invention provides complex rhodium compounds containing rhodium in combination with the ligands carbon monoxide and a plurality of triarylphosphines and having the formulae:

| | |
|---|---|
| $[(aryl_3P)_2Rh(CO)(alkylCN)]_{8-n}X^{+n}M_{12}O_{40}$ | I |
| $[(aryl_3P)_2Rh(CO)(alkylCN)]_{9-n}X^{+n}M_{12}O_{40}$ | II |
| $[(aryl_3P)_2Rh(CO)]_{8-n}X^{+n}M_{12}O_{40}$ | III |
| $[(aryl_3P)_2Rh(CO)]_{9-n}X^{+n}M_{12}O_{40}$ | IV |
| $[(aryl_3P)_2Rh(CO)_3]_{8-n}X^{+n}M_{12}O_{40}$ | V |
| $[(aryl_3P)_2Rh(CO)_3]_{9-n}X^{+n}M_{12}O_{40}$ | VI | wherein alkyl is lower alkyl ($C_1$ to $C_4$), X is an element selected from Periodic Table groups IIIA (such as B) IVA (such as Si, Ge) or VA (such as P, As), and transition elements of Group VIII such as Cu, Ni, Cr, Co, Fe, Mn, Ti, Zr), aryl can be phenyl or phenyl substituted by 1 to 3 lower alkyl ($C_1$ to $C_4$) and lower alkoxy ($C_1$ to $C_4$) groups, M is molybdenum (Mo) or tungsten (W), and n is an integer having a value 2 to 5.

These novel complex rhodium compounds catalyze the hydroformylation of olefins to produce aldehydes, the oxidation of aldehydes to provide carboxylic acids, the oxidation of carbon monoxide to form carbon dioxide, the isomerization of terminal to internal olefins and the oxidation of carbon monoxide by nitric oxide.

In a further aspect, a method of preparing the complex rhodium compounds is disclosed.

The present invention differs from the background art in several respects. The present invention describes oxymetallate catalysts having the general formulae I–VI. The phosphine- and carbonyl-substituted rhodium complexes are combined with or bonded to metal-oxygen clusters having the general formulas $X^{+n}M_{12}O_{40}{}^{-(8-n)}$ and $X^{+n}M_{12}O_{40}{}^{-(9-n)}$.

In contrast to the complex anions taught in U.S. Pat. No. 3,821,311 which are capable of undergoing nucleophilic substitution, Keggin ions are not capable of undergoing nucleophilic substitution. Thus, hydroxide and chloride react with a nucleophilic proton to form water and hydrogen chloride. Keggin ions, in contrast, form hydrated hydronium (i.e., $H_3O^+$ salts) which decompose on attempted removal of water [T. J. R. Weakley, Structure and Bonding 18, 131, (1974)] and $H_{8-n}(X^{+n}M_{12}O_{40})$ species, for example, are not formed.

Not only do the rhodium complexes of this invention catalyze the hydroformylation of olefins to produce aldehydes, they are bifunctional in that they catalyze the further oxidation of the resultant aldehyde to the corresponding carboxylic acid. Thus, the metal oxide portion of the catalyst is chemically active, in contrast to systems in which $WO_3$ is only an inert support material and in contrast to other rhodium-containing compounds in the prior art which catalyze only hydroformylation. Furthermore, the formation of the aldehyde and subsequent oxidation of the aldehyde to the acid can be conducted sequentially in the same reaction vessel and without isolation of the intermediate aldehyde. Moreover, complexes of this invention catalyze the oxidation by nitric oxide of carbon monoxide to carbon dioxide and also catalyze the isomerization of olefins having a terminal double bond to olefins having an internal double bond.

In this application:

"oxymetallate" means a complex ion containing nonconnected oxygen atoms in combination with one or more metal atoms and optionally at least one nonmetallic atom, e.g., $Cr_2O_7{}^{2-}$ or $Mo_7O_{24}{}^{6-}$;

"Keggin ion" means a heteropolyanion which is a discrete charged molecular entity, e.g., $SiW_{12}O_{40}{}^{4-}$;

"Keggin acid" means the hydrated hydronium ($H_3O^+$) salt of a Keggin ion, e.g. $(H_3O)_4SiW_{12}O_{40}$ with water of hydration;

"aryl" means phenyl or phenyl substituted by 1 to 3 lower alkyl or alkoxy ($C_1$ to $C_4$) groups; and "Ph" means phenyl.

DETAILED DESCRIPTION

This invention provide new rhodium oxymetallates and processes for their preparation, the rhodium oxymetallates having general formulae I–VI:

| | |
|---|---|
| $[(aryl_3P)_2Rh(CO)(alkylCN)]_{8-n}X^{+n}M_{12}O_{40}$ | I |
| $[(aryl_3P)_2Rh(CO)(alkylCN)]_{9-n}X^{+n}M_{12}O_{40}$ | II |
| $[(aryl_3P)_2Rh(CO)]_{8-n}X^{+n}M_{12}O_{40}$ | III |
| $[(aryl_3P)_2Rh(CO)]_{9-n}X^{+n}M_{12}O_{40}$, | IV |
| $[(aryl_3P)_2Rh(CO)_3]_{8-n}X^{+n}M_{12}O_{40}$ | V |
| $[(aryl_3P)_2Rh(CO)_3 9_{-n}X^{+n}M_{12}O_{40}$ | VI | where alkyl is lower alkyl ($C_1$ to $C_4$), X is an element having oxidation number n and is selected from groups IIIA, IVA, VA, or VIII in the Periodic Table and M is molybdenum (Mo) or tungsten (W), and n is an integer 2 to 5. Aryl is phenyl, or phenyl substituted by 1 to 3 lower alkyl and alkoxy ($C_1$ to $C_4$) groups. Preferably, in the rhodium oxymetallates of the invention aryl is phenyl, X is phosphorus or silicon, and M is molybdenum or tungsten.

The novel complex compounds are prepared by the following methods:

(a) for compounds of Formulae I and II, reaction, at atmospheric pressure and temperature up to the boiling point of the solvent, of salts of $X^{+n}M_{12}O_{40}{}^{-(8-n)}$ or $X^{+n}M_{12}O_{40}{}^{-(9-n)}$ with salts of $(aryl_3P)_3Rh(CO)^+$ in a mixture of alkylnitrile and ethanol (the solvent ratio can be varied as long as the molar ratio of alkylnitrile:Rh is at least 1:1) to provide $[(aryl_3P)_2Rh(CO)(alkylCN)]_{8-n}X^{+n}M_{12}O_{40}$ or $[(aryl_3P)_2Rh(CO)(alkylCN)]_{9-n}X^{+n}M_{12}O_{40}$; and (b) for compounds of Formulae III and IV, using the same conditions as under (a), reaction of salts of $(aryl_3P)_3Rh(CO)^+$ with salts of $X^{+n}M_{12}O_{40}{}^{-(8-n)}$ or $X^{+n}M_{12}O_{40}{}^{-(9-n)}$ in an organic alcohol to provide directly $[(aryl_3P)_2Rh(CO)]_{8-n}X^{+n}M_{12}O_{40}$ or $[(aryl_3P)_2Rh(CO)]_{9-n}X^{+n}M_{12}O_{40}$; wherein X, aryl, and n are as defined above; alternatively compounds of Formulae I and II can be heated to remove alkylnitrile; and (c) for compounds of Formulae V and VI, reaction of compounds of formulae III and IV with CO to provide $[(aryl_3P)_2R(CO)_3]_{8-n}X^{+n}M^{12}O_{40}$ or $[(aryl_3P)_2R(CO)_3]_{9-n}M_{12}O_{40}$, respectively.

Keggin ion hydrated acids are commercially available from Alfa Chemical Company and Fisher Scientific Co.

Specific examples of rhodium oxymetallates of the invention can be prepared by the method shown in the FLOW CHART below.

FLOW CHART

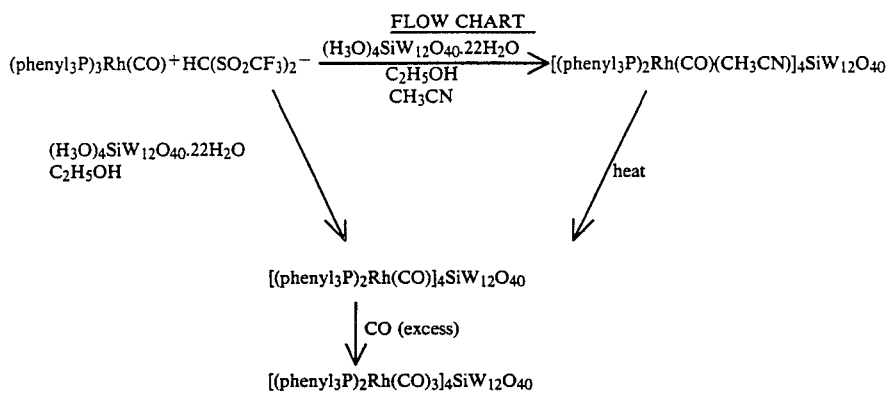

Preparation of the novel rhodium oxymetallates of the invention involves the preparation of certain precursors which are salts of $(aryl_3P)_3Rh(CO)^+$ and which have high solubility in alkylnitrile and optionally in combination with other suitable solvents, e.g., lower aliphatic ($C_1$ to $C_3$) alcohols such as methanol and ethanol. The solvent ratio can be varied as long as the molar ratio of alkylnitrile:Rh is at least 1:1. In these preparations the alkylnitrile, which is normally a liquid, functions as a reactant and a solvent. The requisite solubility is achieved by choice of counterion and for the practice of this invention, $HC(SO_2CF_3)_2^-$ salts are particularly useful. The synthesis of $(aryl_3P)_3Rh(CO)^+HC(SO_2CF_3)_2^-$ and related compounds has been described in detail in U.S. Pat. No. 4,556,720.

In sum, these are prepared by
a. reacting a compound having the formula $[(aryl)_3P]_3Rh(CO)H$, wherein aryl is as defined above, in a 1:1 mole ratio with a fluorochemical acid having the formula $HC(R)(SO_2R_f)_2$, in an organic solvent,
wherein
$R_f$ is a perfluoroalkyl group having 1 to 20 carbon atoms,
R is lower alkyl, phenyl, Cl, H, $SO_2R_f$, or $R_f$,
b. isolating the resulting rhodium(I) coordination compound $[(aryl)_3P]_3Rh(CO)^+HC(SO_2R_f)_2^-$ wherein aryl and $R_f$ are as defined above.

Solutions of $(aryl_3P)_3Rh(CO)^+HC(SO_2CF_3)_2^-$ in a 1:1 mixture of alkylnitrile and ethanol are reacted with solutions of hydrated Keggin ion acids to form $[(aryl_3P)_2Rh(CO)(alkylCN)]_{8-n}X^{+n}M_{12}O_{40}$ or $[(aryl_3P)_2Rh(CO)(alkylCN)]_{9-n}X^{+n}M_{12}O_{40}$. The rhodium oxymetallates thus produced are insoluble in the solvent mixture, can be precipitated and are then isolated by filtration. By hydrated acid, it is meant that all of the negative charge on the Keggin ion is neutralized by an appropriate number of $H_3O^+$ (hydronium) ions and that the resulting hydronium salt contains additional water of solvation. The reaction is illustrated below for the preparation of $[(Ph_3P)_2Rh(CO)(CH_3CN)]_4SiW_{12}O_{40}$:

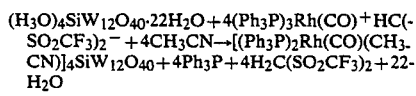

Stoichiometry of the above reaction does not depend on the degree of hydration of the commercially available Keggin ion acids, which, because some of these acids are hygroscopic, is variable, so long as the acid is soluble in the solvent mixture. Other salts, such as those in which some or all of the $H_3O^+$ cations are replaced by other cations such as $Na^+$ may be used so long as the salt is soluble in the solvent or solvent mixture chosen. Lower aliphatic alcohols are suitable as solvents. Methanol and ethanol are preferred since the solubility of $(aryl_3P)_3Rh(CO)^+$ salts decreases with increasing organic chain length. Other alkylnitriles, such as propionitrile and butyronitrile, may be employed as well. Acetonitrile is preferred because of its low cost and because its low boiling point facilitates thermal desolvation as described below. The presence of coordinated acetonitrile in $[(aryl_3P)_2Rh(CO)(CH_3CN)]_4SiW_{12}O_{40}$ was demonstrated by elemental analyses and by infrared spectroscopy. Other salts of $(aryl_3P)_3Rh(CO)^+$ which can be used include those of $BF_4^-$, $SbF_6^-$, $PF_6^-$, $AsF_6^-$, $CF_3CO_2^-$ and $CF_3SO_3^-$ and $N(SO_2CF_3)_2^-$.

When $[(aryl_3P)_2Rh(CO)(alkylCN)]_{8-n}X^{+n}M_{12}O_{40}$ and $[(aryl_3P)_2Rh(CO)(alkylCN)]_{9-n}X^{+n}M_{12}O_{40}$ compounds prepared by the method of this invention are heated under vacuum, alkylnitrile is volatilized or evolved and new compounds having the general formula $[(aryl_3P)Rh(CO)]_{8-n}X^{+n}M_{12}O_{40}$ and $[(aryl_3P)_2Rh(CO)]_{9-n}X^{+n}M_{12}O_{40}$, respectively, are produced. Heat-induced loss of alkylnitriles such as acetonitrile is referred to as thermal desolvation. It may be carried out at atmospheric pressure in the presence of an inert gas such as nitrogen or argon. Use of air is undesirable as the compounds react with oxygen at elevated temperature. Application of a vacuum is helpful because this assists in the removal of the volatile components. Loss of alkylnitrile was confirmed by elemental and infrared spectroscopic analyses of the products.

The temperature employed for the thermal desolvation process is quite critical. Suitable temperatures are chosen on the basis of thermal programmed desorption (TPD) spectroscopy. In this technique, the sample is heated in a mass spectrometer while the ion currents for thermally desorbed molecules are monitored as a function of temperature. Since the ion current is proportional to the amount of material evolved, a temperature which provides the maximum rate of desolvation may be readily selected.

In the case of $[(phenyl_3P)_2Rh(CO)(CH_3CN)]_4SiW_{12}O_{40}$, TPD data show that the peak temperature for loss of acetonitrile is 140° C. and so this is the approximate temperature used for desolvation and conversion of this compound into $[(phenyl_3P)_2Rh(CO)]SiW_{12}O_{40}$. At higher temperatures, loss of carbon monoxide occurs. It should be noted that the TPD profiles for appearance of CO (m/e 28), $C_6H_5$ (m/e 77) and $C_{12}H_{10}$ (m/e 154) are all quite similar, indicating that the breakdown of the triphenylphosphine ligand to give, inter alia, biphenyl, occurs at about the same temperature as that needed for release of carbon monoxide. Other Keggin ions which can be used in this way are, for example, $SiMo_{12}O_{40}^{4-}$, $PW_{12}O_{40}^{3-}$, and $PMo_{12}O_{40}^{3-}$.

An alternative and preferred route to the preparation of compounds of Formulae III and IV which eliminates the need for a thermal desolvation step may be achieved simply by combining alcoholic ($C_1$ to $C_3$) solutions of $(aryl_3P)_3Rh(CO)^+HC(SO_2CF_3)_2^-$ and the Keggin ion. The product precipitates from the reaction mixture and is isolated by filtration or centrifugation. Ethanol and methanol are the preferred solvents for the reasons given above. This synthetic method can also be used with, for example, the Keggin ions $SiW_{12}O_{40}^{4-}$, $SiMo_{12}O_{40}^{4-}$, $PMo_{12}O_{40}^{3-}$ and $PMo_{12}O_{40}^{4-}$. Substitution of tungsten or molybdenum by other elements (see Pope in "Heteropoly and Isopoly Oxymetallates", supra) is permissible, as indicated here by the synthesis, using the same general method, of $[(phenyl_3P)_2Rh(CO)]_4PVMo_{11}O_{40}$ in which one molybdenum atom in the Keggin ion is replaced by vanadium. Vanadium is introduced by use of hydrated $(H_3O)_4PVMo_{11}O_{40}$ prepared by the method of G. A. Tsigdinos et al., Inorg. Chem. 7, 437 (1968). Other anions such as $N(SO_2CF_3)_2^-$, $C_6H_5C(SO_2CF_3)_2^-$, $BF_4^-$, $SbF_6^-$, $CF_3CO_2^-$, $PF_6^-$, $AsF_6^-$, $CF_3SO_3^-$, etc. may be substituted for $HC(SO_2CF_3)_2^-$. Hydronium salts of Keggin ions are the preferred source of the metal oxide anions since these acids have high solubility in alcoholic solvents.

Complex compounds of the type $[(aryl_3P)_2Rh(CO)(alkylCN)]_{8-n}X^{+n}M_{12}O_{40}$, and $[(aryl_3P)_2Rh(CO)]_{8-n}X^{+n}M_{12}O_{40}$, and $[(aryl_3P)_2Rh(CO)_3]_{8-n}X^{+n}M_{12}O_{40}$ prepared according to this invention are yellow or yellow-green powders which are stable towards air and atmospheric moisture. The $[(aryl_3P)_2Rh(CO)(alkylCN)]_{9-n}X^{+n}M_{12}O_{40}$, $[(aryl_3P)_2Rh(CO)]_{9-n}X^{+n}M_{12}O_{40}$, and $[(aryl_3P)_2Rh(CO)_3]_{8-n}X^{+n}M_{12}O_{40}$ compounds have blue or blue-green colors. Compounds of all six classes are insoluble in common organic solvents such as benzene, acetone, chloroform, acetonitrile and tetrahydrofuran but may be dissolved in propylene carbonate.

Typical examples of complex compounds having formulae I to VI include:

| | |
|---|---|
| $[(Ph_3P)_2Rh(CO)(C_2H_5CN)]_3PMo_{12}O_{40}$ | I |
| $\{[(m-tolyl)_3P]_2Rh(CO)(C_3H_7CN)\}_4SiW_{12}O_{40}$ | |
| $[(Ph_3P)_2Rh(CO)(CH_3CN)]_5FeW_{12}O_{40}$ | |
| $[(Ph_3P)_2Rh(CO)(C_2H_5CN)]_5CoW_{12}O_{40}$ | |
| $[(Ph_3P)_2Rh(CO)(C_3H_7CN)]_3PMo_{12}O_{40}$ | |
| $\{[(p-tolyl)_3P]_2Rh(CO)(CH_3CN)\}_5SiW_{12}O_{40}$ | II |
| $\{[(p-tolyl)_3P]_2Rh(CO)(C_2H_5CN)\}_4PMo_{12}O_{40}$ | |
| $[(Ph_3P)_2Rh(CO)(CH_3CN)]_4PMo_{12}O_{40}$ | |
| $[(Ph_3P)_2Rh(CO)]_4SiW_{12}O_{40}$ | III |
| $[(Ph_3P)_2Rh(CO)]_5BW_{12}O_{40}$ | |
| $[(Ph_3P)_2Rh(CO)]_4GeW_{12}O_{40}$ | |
| $[(Ph_3P)_2Rh(CO)]_5MnW_{12}O_{40}$ | |
| $\{[(p-CH_3OPh)_3P]_2Rh(CO)\}_3AsMo_{12}O_{40}$ | |
| $\{[(m-tolyl)_3P]_2Rh(CO)\}_4PMo_{12}O_{40}$ | IV |
| $[(Ph_3P)_2Rh(CO)]_4PW_{12}O_{40}$ | |
| $[[(p-tolyl)_3P]_2Rh(CO)]_3]_4SiMo_{12}O_{40}$ | V |
| $[\{[2,4,5-(CH_3)_3C_6H_2]P\}_2Rh(CO)_3]_3PW_{12}O_{40}$ | |
| $[(Ph_3P)_2Rh(CO)_3]_5CrW_{12}O_{40}$ | |
| $[(Ph_3P)_2Rh(CO)_3]_5FeW_{12}O_{40}$ | |
| $[(Ph_3P)_2Rh(CO)_3]_4PMo_{12}O_{40}$ | VI |
| $\{[(p-tolyl)_3P]_2Rh(CO)_3\}_5SiMo_{12}O_{40}$ | |
| $\{[(m-tolyl)_3P]_2Rh(CO)_3\}_4PMo_{12}O_{40}$ | |

New complexes having the general formulae I through VI are useful as catalysts for the manufacture of organic compounds. Specifically, the new compositions of matter are useful for catalytic isomerization of terminal olefins, for the conversion by hydroformylation of olefins to aldehydes, and for the oxydation of aldehydes to carboxylic acids. Complexes of formulae III to VI are also useful for catalyzing the oxidation by nitric oxide of carbon monoxide to produce carbon dioxide.

Isomerization of termination olefins to internal olefins, wherein a C—C double bond originally located between the carbon atom at the end of a chain of carbon atoms is rearranged to an internally-located double bond, as is illustrated by the rearrangement of 1-hexene. When this olefin was heated with a suspension of $[(Ph_3)_2Rh(CO)]_4SiW_{12}O_{40}$ in toluene, quantitative conversion to a mixture of cis- and trans-2-hexene, accompanied by a small amount of 3-hexene, occurred.

As is known in the art, the rates of hydroformylation in the absence of a catalyst are uselessly slow. Compounds of the general formulae I–VI, produced according to this invention are useful catalysts for acceleration of the rates of hydroformylation. In the case used here for illustrative purposes, of 1-hexene, the isomeric aldehydes, heptanal and 2-methylhexanal, may be produced depending on whether the carboxaldehye or —C(O)H group is added to the terminal carbon atom or to the carbon atom adjacent to it. Thus when 1-hexene and a suspension of $[(Ph_3P)_2Rh(CO)]_4SiW_{12}O_{40}$ in the inert solvent toluene were contacted with a mixture of hydrogen and carbon monoxide, both aldehydes were produced. Careful analysis of the product mixture also revealed that a third aldehyde, 2-ethylpentanal, was present. It is believed that 2-ethylpentanal arises from hydroformylation of 3-hexene produced by isomerization of the starting olefin, 1-hexene.

When the mixture of aldehydes, produced as described above, is allowed to stand at room temperature in air in the presence of the same catalyst, either added independently or recovered from the hydroformylation reaction mixture, oxidation of the aldehydes occurs and the corresponding carboxylic acids, heptanoic acid, 2-methylhexanoic acid and 2-ethylpentanoic acid, is formed in essentially quantitative yield. No such oxidation occurs in the absence of the catalyst. Therefore, compounds of the general formula I–VI as illustrated above are bifunctional catalysts because they are able to catalyze two successive organic reactions which feature distinguishes them from the catalysts taught in U.S. Pat. No. 3,821,311.

To achieve a practical synthesis of carboxylic acids from olefins it is not necessary that the intermediate aldehyde be isolated. It is sufficient to contact the olefin, catalyst and a suitable dispersing medium such as an aliphatic or aromatic hydrocarbon (generally, $C_5$ to $C_{20}$), successively with a mixture of carbon monoxide and hydrogen, to prepare the aldehyde and then with oxygen or air to oxidize the resultant aldehyde to the corresponding acid.

The tricarbonyl analogues of complex compounds III and IV above, have formulae, for example $[(Ph_3P)_2Rh(CO)_3]_4SiW_{12}O_{40}$, $[(Ph_3P)_2Rh(CO)_3]_3PMo_{12}O_{40}$, and $[(Ph_3P)_2Rh(CO)_3]_3SiMo_{12}O_{40}$. They are prepared by solid-gas reactions between carbon monoxide and the corresponding [(Ph$_3$P)$_2$Rh(CO)] (Keggin ion) compounds. The tricarbonyl analogues are kinetically and thermodynamically stable compounds which share the same set of useful properties as the monocarbonyl analogues with respect to catalytic activation of CO in hydroformylation reactions. On prolonged standing or under vacuum the tricarbonyl analogues can lose CO and revert to the starting materials.

Various modifications and alterations of this invention will become apparent to those skilled in the art without departing from the scope and spirit of this invention, and it should be understood that this invention is not to be unduly limited to the following illustrative examples. Unless otherwise stated, all percentages given are percentages by weight.

All temperatures are reported in degrees centigrade and all percents are by weight unless otherwise stated. Each of the new transition metal compounds prepared in this invention were analyzed for at least three of the elements selected from carbon, hydrogen, nitrogen, phosphorus and rhodium and by infrared spectroscopic analysis. In the Examples, Ph means phenyl.

EXAMPLE 1

Synthesis of [(Ph$_3$P)$_2$Rh(CO)(CH$_3$CN)]$_4$SiW$_{12}$O$_{40}$

To a solution of 0.59 g (Ph$_3$P)$_3$Rh(CO)$^+$HC(SO$_2$CF$_3$)$_2^-$ in 10 mL of a mixture of 3 volumes of acetonitrile and 1 volume of ethanol was added 0.41 g hydrated (H$_3$O)$_4$SiW$_{12}$O$_{40}$ (Fisher Scientific Co., Fairlawn, N.J.) in 15 mL of the same solvent mixture. A gummy precipitate separated which solidified on vigorous stirring. This precipitate was collected on a filter, was washed with fresh solvent mixture and was dried at 30° C. under vacuum. The yield of [(Ph$_3$P)$_2$Rh(CO)(CH$_3$CN)]$_4$SiW$_{12}$O$_{40}$ was 0.63 g. Similar syntheses were performed using (Ph$_3$P)$_3$Rh(CO)$^+$BF$_4^-$ [prepared as described by P. Legzdins, R. W. Mitchell, G. L. Rempel, J. D. Ruddick and G. Wilkinson, J. Chem. Soc. (A), 3322 (1970)].

EXAMPLE 2

Thermal Desolvation of [(Ph$_3$P)$_2$Rh(CO)(CH$_3$CN)]$_4$SiW$_{12}$O$_{40}$

A 1.65 g sample of [(Ph$_3$P)$_2$Rh(CO)(CH$_3$CN)]$_4$SiW$_{12}$O$_{40}$, prepared according to Example 1, was placed in a glass flask which was then attached to a vacuum line. After evacuation to a pressure of about 10$^{-4}$ mm Hg., the flask and its contents were heated at 150° C. for 22 hours with continuous pumping. Upon cooling, 1.55 g of [(Ph$_3$P)$_2$Rh(CO)]$_4$SiW$_{12}$O$_{40}$ remained in the flask.

EXAMPLE 3

Direct Synthesis of [(Ph$_3$P)$_2$Rh(CO)]$_4$SiW$_{12}$O$_{40}$

To a solution of 1.3 g (Ph$_3$P)$_3$Rh(CO)$^+$HC(SO$_2$CF$_3$)$_2^-$ (see U.S. Pat. No. 4,556,720, Ex. 9, for preparation) in 30 mL warm absolute ethanol was added dropwise with vigorous stirring a solution of 0.82 g hydrated (H$_3$O)$_4$SiW$_{12}$O$_{40}$ in 5 mL of ethanol. The product, which precipitated from the reaction mixture, was collected on a filter, washed with more ethanol and vacuum dried as in Example 1. The yield was 1.2 g. Elemental analyses and spectroscopic properties of this product matched those of the material prepared in Example 2.

EXAMPLE 4

Isomerization of 1-hexene

In a glass tube were placed 0.03 g [(Ph$_3$P)$_2$Rh(CO)]$_4$SiW$_{12}$O$_{40}$, 2 mL toluene and 0.6 mL 1-hexene. The mixture was degassed by two freeze-pump-thaw cycles, brought to atmospheric pressure under argon, then stirred and heated at 100° C. for 12 hours. After cooling to room temperature, the insoluble catalyst was removed by filtration. The filtrate was analyzed by 13-C NMR spectroscopy and found to contain 60% trans-2-hexene, 25% cis-2-hexene, 9% trans-3-hexene, 2% cis-3-hexene and 5% 1-hexene.

EXAMPLE 5

Hydroformylation and hydroformylation-oxidation

Three isomers of n-hexene were independently hydroformylated and the products oxidized to determine selectivity.

A mixture of 1 mL of the olefin, 10 mL toluene and 0.1 g [(Ph$_3$P)$_2$Rh(CO)]$_4$SiW$_{12}$O$_{40}$ were placed in an autoclave. It was twice evacuated and backfilled to about atmospheric pressure with a 1:1 mixture of carbon monoxide and hydrogen. The CO—H$_2$ pressure was then increased to 145 kPa (1000 psig), the autoclave heated for 3 hrs. at about 100° C., and cooled to room temperature. The gas phase was vented. A sample of the liquid remaining was removed for gas chromatography, mass spectroscopy (GC-MS) analysis. The samples was immediately filtered through a sintered glass disc to remove any entrained catalyst.

Oxidation of the aldehydes produced in the above reaction was carried out as follows. Air, at a pressure of 94 kPa (650 psig), was introduced into the autoclave which was then heated at 100° C. for 4 hours. After this time, the autoclave was cooled to room temperature and the contents removed. Analyses of the product were carried out by gas chromatography and mass spectrometry. TABLE I, below, indicates the distribution of aldehydes among the isomeric heptanal, 2-methylhexanal and 2-ethylpentanal and of the carboxylic acids among the isomeric heptanoic acid, 2-methylhexanoic acid and 2-ethylpentanoic acid. The absolute yields of heptanal, 2-methylhexanal and 2-ethylpentanal from 1-hexene in this example were 43.4, 27.7 and 5.2% respectively.

TABLE I

| | Normalized Yields of Aldehydes and Acids Derived from Hexenes | | | | | |
|---|---|---|---|---|---|---|
| Substrate | Heptanal | 2-Methylhexanal | 2-Ethylpentanal | Heptanoic Acid | 2-Methylhexanoic acid | 2-Ethylpentanoic acid |
| 1-hexene | 56.6% | 36.0% | 7.4% | 52.4% | 40.0% | 7.6% |
| 2-hexene | 13.4% | 56.6% | 30.0% | 8.9% | 52.7% | 38.4% |
| 3-hexene | 9.8% | 39.7% | 50.5% | 8.4% | 35.2% | 56.4% |

Similar reactions were carried out using [(Ph$_3$P)$_2$Rh(CO)]$_4$PVMo$_{11}$O$_{40}$, [(Ph$_3$P)$_2$Rh(CO)]$_4$SiMo$_{12}$O$_{40}$, [(Ph$_3$P)$_2$Rh(CO)]$_3$PW$_{12}$O$_{40}$ and [(Ph$_3$Rh(CO)]$_3$PMo$_{12}$O$_{40}$ as catalysts. Normalized yields of isomeric aldehydes and carboxylic acid are given in TABLE II, below. By normalized yield is meant the mole fraction, expressed as a percentage, of a given aldehyde relative to the total number of moles of aldehyde produced.

EXAMPLE 6

Hydroformylation using $[(Ph_3P)_2Rh(CO)(CH_3CN)]_{8-n}X^{+n}M_{12}O_{40}$ catalysts Hydroformylation of 1-hexene was carried out as described in Example 5 using independently as catalysts $[(Ph_3P)_2Rh(CO)(CH_3CN)]_3PW_{12}O_{40}$ and $[(Ph_3P)_2Rh(CO)(CH_3CN)]_3PMo_{12}O_{40}$. Normalized yields of heptanal, 2-methylhexanal and 2-ethylpentanal in the two experiments were 46.0, 40.6 and 11.4% and 46.3, 41.6 and 12.1% respectively.

EXAMPLE 7

Hydroformylation-oxidation of 1,3-butadiene

Butadiene was treated with a mixture of $H_2$ and CO then air as described in Example 5, using $[(Ph_3P)_2Rh(CO)]_4SiMo_{12}O_{40}$ as the catalyst. 13-C NMR and GC-MS analyses showed that pentanoic acid and 2-methylbutanoic acid were formed in a 2:1 ratio.

EXAMPLE 8

Synthesis of $[(Ph_3P)_2Rh(CO)(CH_3CN)]_4PMo_{12}O_{40}$

A deep blue solution containing $PMo_{12}O_{40}^{4-}$ was prepared by addition of 1.1 mL of a deoxygenated 0.2M solution of $NaBH_4$ in ethanol to 0.21 mmole (0.38 gm) of hydrated $(H_3O)_3PMo_{12}O_{40}$ in 5 mL ethanol under nitrogen. After stirring for 5 min., a solution of 1.0 g $(Ph_3P)_3Rh(CO)+HC(SO_2CF_3)_2^-$ in 8 mL deoxygenated 3:1 (v/v) ethanol-acetonitrile was added dropwise. The product separated as a blue-green powder which was collected on a filter, washed with ethanol then vacuum dried, yield 0.6 g. Hydroformylation-oxidation of 1-hexene as previously described yielded 2-ethylpentanoic acid, 2-methylhexanoic acid and heptanoic acid in a 10:35:50 ratio; hexane was formed in less than 1% yield.

EXAMPLE 9

Synthesis of $[(Ph_3P)_2Rh(CO)]_4PMo_{12}O_{40}$

This compound was prepared by the method used in Example 8 except that the $(Ph_3P)_3Rh(CO)+HC(SO_2CF_3)_2^-$ was added as a solution in pure deoxygenated ethanol. Hydroformylation of 1-hexene using this catalyst gave 2-ethylpentanal, 2-methylhexanal and 1-heptanal in a 3:31:60 ratio. The yield of the hydrogenation product, n-hexane, was less than 1%.

EXAMPLE 10

Oxidation of carbon monoxide to carbon dioxide

A 0.035 g sample of $[(Ph_3P)_2Rh(CO)]_4SiW_{12}O_{40}$ was placed in a 10.2×0.6 cm (4×¼ in.) glass tube fitted with a stopcock. The vessel was evacuated then filled to a pressure of 160 mm Hg with a 1:1 mixture of CO and NO. After standing at room temperature for three days, the gas phase was analyzed by gas chromatography and mass spectrometry which revealed that 12% of the CO had been converted to $CO_2$; only trace amounts of $N_2O$ were detected.

EXAMPLE 11

A 0.2 gm sample of $[(Ph_3P)_2Rh(CO)]_4SiW_{12}O_{40}$ was placed in a glass-lined pressure vessel. This was evacuated, backfilled to a pressure of 200 psi with carbon monoxide. After standing at room temperature overnight, the carbon monoxide was vented and the product, 0.2 gm, removed. Spectroscopic analysis showed that conversion to $[(Ph_3P)_2Rh(CO)_3]_4SiW_{12}O_{40}$ was approximately 50%.

A similar experiment was carried out in which the pressure of carbon monoxide was 2,000 psi. In this case, spectroscopic analysis showed that the yield of $[(Ph_3P)_2Rh(CO)_3]_4SiW_{12}O_{40}$ was quantitative. The compound loses carbon monoxide on application of a vacuum or, more slowly, on standing in air to reform the starting material.

The compound $[(Ph_3P)_2Rh(CO)_3]_4SiW_{12}O_{40}$ was also produced when a 1:1 mixture of hydrogen and carbon monoxide at a pressure of 1,000 psi was substituted for pure carbon monoxide. This compound can be used as a hydroformylation-oxidation catalyst for 1-hexene.

EXAMPLE 12

A 0.17 g portion of $[(Ph_3P)_2Rh(CO)]_4PMo_{12}O_{40}$, prepared according to Example 9, was treated with carbon monoxide as in Example 11. Infrared analysis of the product indicated that $[(Ph_3P)_2Rh(CO)_3]_4PMo_{12}O_{40}$ formed in approximately 60% yield.

TABLE II

| | Normalized Yields of Aldehydes and Acids from 1-Hexene | | | | | |
|---|---|---|---|---|---|---|
| Catalyst | Heptanal | 2-Methyl hexanal | 2-Ethyl pentanal | Heptanoic acid | 2-Methyl hexanoic acid | 2-Ethyl pentanoic acid |
| $[(Ph_3P)_2Rh(CO)]_4PVMo_{11}O_{40}$ | 64% | 33% | 3% | trace | trace | trace |
| $[(Ph_3P)_2Rh(CO)]_4PVMo_{11}O_{40}$ after air oxidation | trace | trace | trace | 66% | 31% | 3% |
| $[(Ph_3P)_2Rh(CO)]_4SiMo_{12}O_{40}$ | 56% | 32% | 5% | 3% | 3% | trace |
| $[(Ph_3P)_2Rh(CO)]_4SiMo_{12}O_{40}$ after air oxidation | trace | trace | trace | 61% | 33% | 6% |
| $[(Ph_3P)_2Rh(CO)]_3PW_{12}O_{40}$ | 45% | 35% | 9% | 7% | 5% | trace |
| $[(Ph_3P)_2Rh(CO)]_3PW_{12}O_{40}$ after air oxidation | trace | trace | trace | 53% | 38% | 9% |
| $[(Ph_3P)_2Rh(CO)]_3PMo_{12}O_{40}$ | 50% | 35% | 7% | 4% | 3% | trace |
| $[(Ph_3P)_2Rh(CO)]_3PMo_{12}O_{40}$ after air oxidation | trace | trace | trace | 54% | 38% | 8% |

EXAMPLE 13

Synthesis of $[(Ph_3P)_2Rh(CO)(C_3H_7CN)]_3PW_{12}O_{40}$

To a solution of 0.6 g $(Ph_3P)_3Rh(CO)+HC(SO_2CF_3)_2^-$ in 12 mL of 1 volume of butyronitrile and 1 volume of methanol was added dropwise with stirring 0.5 g hydrated $(H_3O)_3PW_{12}O_{40}$ in 3 mL of the same solvent mixture. The solid product which separated was collected on a filter, washed with methanol and vacuum dried at 30° C. The yield of $[(Ph_3P)_2Rh(CO)(C_3H_7CN)]_3PW_{12}O_{40}$, identified by elemental and spectroscopic analyses, was 0.7 g.

Various modifications and alterations of this invention will become apparent to those skilled in the art without departing from the scope and spirit of this invention, and it should be understood that this invention is not to be unduly limited to the illustrative embodiments set forth herein.

I claim:

1. A method comprising the steps:
   (a) reacting $(aryl_3P)_3Rh(CO)^+HC(SO_2CF_3)_2^-$ with a hydrated Keggin ion acid $(H_3O)_{8-n}X^{+n}M_{12}O_{40}$ or $(H_3O)_{9-n}X^{+n}M_{12}O_{40}$ in the presence of an alkylnitrile to form a rhodium oxymetallate $[(aryl_3P)_2Rh(CO)(alkylCN)]_{8-n}X^{+n}M_{12}O_{40}$ or $[(aryl_3P)_2Rh(CO)(alkylCN)]_{9-n}X^{+n}M_{12}O_{40}$, wherein
   alkyl is lower alkyl ($C_1$ to $C_4$),
   aryl is phenyl or phenyl substituted by 1 to 3 lower alkyl or alkoxy groups,
   X is a transition element of Periodic Table groups IIIA, IVA, or VA,
   M is Mo or W, and
   n is an integer having a value of 2 to 5, and
   (b) isolating said resulting rhodium oxymetallate.

2. The method according to claim 1 further comprising the step, after step (a) or (b),
   (c) causing said rhodium oxymetallate to undergo thermal desolvation to provide a second rhodium oxymetallate having the formula $[(aryl_3P)_2Rh(CO)]_{8-n}X^{+n}M_{12}O_{40}$ or $[(aryl_3P)_2Rh(CO)]_{9-n}X^{+n}M_{12}O_{40}$ wherein aryl is phenyl or phenyl substituted by 1 to 3 lower alkyl or alkoxy groups, and
   (d) isolating said second rhodium oxymetllate.

3. The method according to claim 1 further comprising said alkylnitrile dissolved in a solvent.

4. The method according to claim 2 further comprising the step of reacting said second rhodium oxymetallate with carbon monoxide to form a tricarbonyl analogue of said oxymetallate.

5. A method comprising the steps of:
   (a) reacting an alcohol solution of a salt of $(aryl_3P)_3Rh(CO)^+$ and a salt of $XM_{12}O_{40}^{-(8-n)}$, wherein aryl is phenyl or phenyl substituted by 1 to 3 lower alkyl or alkoxy groups, X is a transition element of Periodic Table groups IIIb, IVb, or Vb, and M is Mo or W, to provide a rhodium oxymetallate of the formula $[(aryl_3P)_2Rh(CO)]_{8-n}X^{+2}M_{12}O_{40}$ or $[(aryl_3P)_2Rh(CO)]_{9-n}X^{+n}M_{12}O_{40}$ wherein n is an integer having a value of 2 to 5, and
   (b) isolating the resulting rhodium oxymetallate.

6. The method according to claim 5 further comprising the step of reacting said resulting oxymetallate with carbon monoxide to form a tricarbonyl analogue of said oxymetallate.

* * * * *

UNITED STATES PATENT AND TRADEMARK OFFICE
CERTIFICATE OF CORRECTION

PATENT NO. : 4,788,308

DATED : November 29, 1988

INVENTOR(S) : Allen R. Siedle

It is certified that error appears in the above-identified patent and that said Letters Patent is hereby corrected as shown below:

Col. 4, line 14, delete "$Rh(CO)_3 9_{9-n}$" and insert therefor -- $Rh(CO)_3]_{9-n}$ --.

Signed and Sealed this

Eighteenth Day of July, 1989

Attest:

DONALD J. QUIGG

Attesting Officer

Commissioner of Patents and Trademarks